United States Patent [19]
Bittins et al.

[11] Patent Number: 5,726,321
[45] Date of Patent: Mar. 10, 1998

[54] PROCESS FOR CARRYING OUT GAS/LIQUID REACTIONS UNDER AVOIDANCE OF A CONTINUOUS GAS PHASE

[75] Inventors: Klaus Bittins, Frankenthal; Marc Heider, Neustadt; Martin Schmidt-Radde, Beindersheim; Jochen Kellenbenz, Bad Dürkheim; Kurt Josef Wagner, Römerberg; Peter Zehner, Ludwigshafen; Stefan Berg, Frankenthal, all of Germany

[73] Assignee: BASF Aktiengesellschaft, Ludwigshafen, Germany

[21] Appl. No.: 620,940

[22] Filed: Mar. 22, 1996

[30] Foreign Application Priority Data

Mar. 24, 1995 [DE] Germany ............ 195 10 890.6
Nov. 23, 1995 [DE] Germany ............ 195 43 636.9

[51] Int. Cl.⁶ .......... C07D 233/54; C07C 41/00; C07C 43/00; C07C 35/08; C07C 35/18; C07C 31/18

[52] U.S. Cl. .......... 548/335.1; 422/117; 422/227; 528/126; 528/212; 528/214; 528/215; 568/672; 568/679; 568/680; 568/822; 568/831; 568/835; 568/852; 585/951

[58] Field of Search .......... 548/335.1; 585/951; 528/176, 214, 215, 212; 422/117, 227; 568/822, 835, 831, 852, 853, 672, 679, 680

[56] References Cited

U.S. PATENT DOCUMENTS 3,957,888  5/1976  Reiss et al. .......... 568/852 X
4,482,696  11/1984  Schuster et al. .......... 528/212

FOREIGN PATENT DOCUMENTS 2395977  1/1979  France.
2421407  10/1975  Germany.
3206661  9/1983  Germany.
833664  4/1960  United Kingdom.

OTHER PUBLICATIONS

Ullmann's Encyc. of Ind. Chem., vol. A1, 5th Edition, pp. 101–105 (1972).

Schildberg et al, Chem.–Ing. Tech 66 (1994),pp. 1389–1392.

Miller, Acetylene, Ernest Benn Limited (1965) vol. 1, pp. 485–506.

Nedwick, Ind. & Eng. Chem. Process Des. & Develop., vol. 1, No. 2, Apr. 1962, pp. 137–141.

Hanford et al, Ind. & Eng. Chem, vol. 40, No. 7, Jul. 1948 pp. 1171–1177.

*Primary Examiner*—Floyd D. Higel
*Attorney, Agent, or Firm*—John H. Shurtleff

[57] ABSTRACT

Process for carrying out gas/liquid reactions at from (−50°) to 300° C. and from 0.1 to 100 bar by carrying out the reaction in the absence of a continuous gas phase, and, as a special case, a process for the batchwise reaction of acetylene in the liquid phase at from 0° to 300° C. and from 2 to 30 bar, in which acetylene is introduced a) in the absence of a continuous gas phase and b) under isobaric conditions to a degree of saturation of from 5 to 100%.

12 Claims, No Drawings

PROCESS FOR CARRYING OUT GAS/LIQUID REACTIONS UNDER AVOIDANCE OF A CONTINUOUS GAS PHASE

The present invention relates to a process for carrying out gas/liquid reactions with avoidance of a continuous gas phase.

DE-A-32 06 661 discloses a process for avoiding a continuous gas phase by means of a jet. If this jet fails, this leads to separation of gas and liquid. The resulting gas phase must consequently be removed from the explosion area in a very short time by flushing with inert gas.

DE-A-24 21 407 adds a process for avoiding a continuous gas phase by regulating the gas feed to values below the saturation limit, as an additional safety element.

The process described in DE-A-24 21 407 is suitable, in the version described, only for continuous processes. If batchwise reactions are required, for example because of the need for complete conversion, this process is unsuitable. The batchwise process described in DE-A-32 06 661 can be used only for systems which exhibit only a small volume increase in the course of reaction. This is due to the inert gas hold-up which is firmly predetermined before the beginning of the reaction and corresponds to the maximum possible volume increase.

Acetylene can be used industrially for a large number of products (Ullmann Vol. A1, 5th edition, pages 101 to 105). Special safety precautions are required when handling acetylene since gaseous acetylene tends to decompose under pressure (Chem.-Ing.-Tech. 66 (1994), 1389–1392; S. A. Miller, Acetylene, Ernest Benn Limited 1965, Vol. 1, pages 485 to 506). In particular, the catalysts used for the various reactions initiate such decomposition if they accumulate in the gas space of the reactors used.

Ind. Eng. Chem. Proc. Design & Dev. 1 (1962), 137–141, recommends first dissolving acetylene in a separate saturator in the substance to be reacted and a suitable solvent and then reacting this solution in a reactor. In this procedure, the pressure must be chosen so that a gas phase in the reactor can be ruled out, which results in the use of suitable high-pressure apparatuses. Moreover, suitable solvents must be used in this process, and these solvents are expensive to separate off. If the process described there is carried out as a continuous process, the amount of acetylene to be fed to the reactor is virtually constant and an acetylene gas phase in the reactor owing to the introduction of a possibly excessively large amount of acetylene can be avoided.

In the batchwise reaction of acetylene, however, this procedure is extremely difficult since the absorption of acetylene as a result of the reaction is not constant as a function of time but the acetylene concentration in the reactor cannot be controlled. Owing to the different solubilities of acetylene in starting materials and end products, the amount of acetylene soluble in the reactor content is moreover subject to constant changes. In addition, for batchwise reactions the process described has the disadvantage that large amounts of liquid have to be circulated.

Batchwise reactions with acetylene under superatmospheric pressure are therefore carried out in the presence of an acetylene gas phase (for example Ind. Eng. Chem. 40 (1948), 1171–1177). Owing to the danger of decomposition of compressed acetylene, which is described above, such a process requires very expensive safety measures, but decomposition cannot be completely ruled out as a result of these measures. However, batchwise reactions with acetylene under superatmospheric pressure are required in particular when it is intended to achieve virtually complete conversion of the starting material. This may be the case, for example, when starting material and product can be separated only at very great expense, if at all.

It is an object of the present invention to remedy the abovementioned disadvantages, in particular to provide a safe process for batchwise reactions with acetylene under superatmospheric pressure, which is suitable for a large number of products and reactions.

We have found that this object is achieved by a novel and improved process for carrying out gas/liquid reactions at from (−50°) to 300° C. and from 0.1 to 100 bar, wherein the reaction is carried out in the absence of a continuous gas phase, and, as a special case, a process for the batchwise reaction of acetylene in the liquid phase at from 0° to 300° C. and from 2 to 30 bar, in which acetylene is introduced into the liquid phase in the absence of a gas phase under isobaric conditions to a degree of saturation of from 5 to 100%.

The avoidance of a continuous gas phase may be essential or desirable both because of undesired secondary reactions in the gas phase and because of a high potential danger. The potential danger results from the possibility of spontaneous decomposition in the gas phase, or from the very vigorous (for example explosive) reaction of the gaseous substance with reactants present in the reactor system.

The novel process can be carried out as follows:

At from (−50°) to 300° C. and from 0.1 to 100 bar, the liquid reactant can be reacted with the gaseous reactant in the absence of a continuous gas phase in the reactor or in a reactor cascade.

The continuous gas phase is understood as meaning gas spaces within the reaction space whose size goes beyond individual discrete bubbles or small bubbles.

The product stream is as a rule continuously taken off at the highest point of a reactor (for example, of any reactor of a cascade). Any resulting gas bubbles, which may arrive at the top of the reactor, are as a rule immediately removed from the reactor system by the liquid stream.

After exit from the reactor, the operating parameters—for example in a downstream phase separator—are chosen so that this region is in a safe state. This can be effected by reducing pressure and/or temperature and/or by flushing with an inert gas, such as nitrogen, argon, carbon dioxide or steam, preferably nitrogen or carbon dioxide, particularly preferably nitrogen.

In addition to this procedure for avoiding a continuous gas phase, two further supplementary measures—alone or in combination—may be taken:

a) The regulation of the gas concentration (saturation) in the reactor discharge is controlled, as a rule, at from 5 to 100%, preferably at values below the maximum gas solubility, such as from 10 to 95%, particularly preferably from 20 to 80%, in particular from 30 to 80%, especially from 40 to 70%. This is sufficient to prevent the formation of free gas bubbles in the consequently undersaturated liquid, so that the top of the reactor is as a rule free of bubbles.

The determination of the concentration of the gaseous component and hence the regulation of the gas feed are preferably effected by direct measurement in the discharge line or by the simple determination of the exit gas flow after let down, as described below. The exit gas flow resulting at let down is determined by the magnitude of the discharge flow, the amount of gas dissolved therein and the pressure drop at let down. The gas concentration in the discharge line can be determined from the ratio of the exit gas flow to the liquid flow at constant pressure drop. If, owing to the large internal and external circulation flows, the reactor can be regarded as ideally mixed, the gas concentration in the reactor itself is thus also known and can be regulated to a predetermined ideal value, below the saturation limit.

b) With a suitable arrangement of a jet nozzle at the top of the reactor, preferably in the reactor cover, the liquid momentum can be used for redispersing the gas. If relatively large bubbles reach the top of the reactor, they are broken up again. In this procedure, a closed gas phase can form only at high gas loads, even on failure of the continuous flow through the reactor.

In order to be able to realize the required continuous flow through the reaction space in batchwise reactions too, in the batchwise case the reactor system comprises, in addition to the reactor (the reactor cascade), as a rule an equilibration container which acts as the phase separator and is to be rendered safe by suitable measures (pressure reduction, temperature reduction, flushing with inert gas). This can compensate for a volume increase in the course of the reaction. If complete conversion is desired in the reactions carried out, the equilibration container should preferably be converted into a cascade by means of baffles or subdivision. A part-stream is recycled continuously from the equilibration container into the reaction space. The amount of the stream recycled from the equilibration container per unit time is not critical. It should be adapted to the reaction rate and should be about 0.1 to 10 times the amount, based on the total reaction time, of the reactor content.

The reaction can be carried out to any desired conversion, which can be monitored, for example, by continuous analysis of the discharge stream. Complete conversion of reactor content and equilibration container in the batchwise case is also possible and frequently desirable in order to avoid subsequent separation problems.

A nozzle may be used for compressing and dispersing the gas. This ensures a very fine distribution of the gas bubbles and hence a large phase interface at high turbulence, with the result that the gas is rapidly dissolved in the liquid. The nozzle may alternatively be arranged at the base or at the top of the reactor, and a concentric immersion tube should preferably be installed in the latter case. The arrangement of the nozzle at the highest point of the reactor has the advantage that, if the reaction comes to a stop, no liquid can rise back into the gas-conveying part of the nozzle. The use of a self-aspirating nozzle constitutes an additional, integrated safety means, since no more gas can be sucked in if the pump and hence the liquid jet fail, for example, in the event of a fault.

A suitable bubble detector can be installed as a further safety means in the discharge line before possible pressure relief.

The novel process is suitable for a large number of gas/liquid reactions. Examples of gaseous reactants which have a high potential danger and are therefore particularly suitable are:

acetylene and higher homologs; ketenes; ethylene oxide; propylene oxide and higher homologs; acrolein; oxygen; chlorine; chlorine dioxide; hydrazine; hydrazoic acid.

When the integrated reactor safety concept described is used, an abrupt pressure and temperature increase can be reliably avoided. This leads to greater operational safety, shorter down times and lower product losses. Compared with intrisically safe reaction systems, the novel process comprises exclusively simple apparatuses which no longer need to be designed for the explosion pressure but only for a pressure level adapted to the operating pressure. This results in lower capital costs.

For the reaction with acetylene, the following procedure may be used according to the invention:

Acetylene, preferably finely or very finely distributed, can be introduced into the liquid reaction mixture in a closed reaction space (for example a reactor) in the absence of a gas phase at from 0° to 300° C., preferably from 20° to 200° C., under isobaric conditions, ie. at constant or virtually constant pressure, the pressure fluctuations being from 0 to 20%, preferably from 0 to 10%, particularly preferably from 0 to 5%, in particular from 0 to 2%, of the established pressure. The pressure may be as a rule from 2 to 30, preferably from 10 to 25, particularly preferably from 15 to 20, bar.

In a preferred embodiment, a jet reactor is completely filled with the reaction mixture and a continuous liquid stream is recycled to the reactor from an equilibration container with the aid of a pump. The overflow caused by this and by the increase in volume as a result of the reaction is released at the top of the reactor into the equilibration container with the aid of a control valve which keeps the reactor pressure constant, and the amount of said overflow is measured. The amount of the acetylene escaping during this process is likewise measured, providing direct information about the saturation of the reactor content with acetylene. A ratio which should correspond to a setpoint value is determined using the formula ratio=amount of acetylene in the overflow/amount of overflow.

If the ratio determined is greater than the setpoint value, the acetylene feed is decreased; if it is less than said setpoint value, said feed is increased. The maximum solubility of acetylene in the starting materials and reaction products under reaction conditions can be determined in separate experiments by methods known to a person skilled in the art, and the setpoint value can be derived from said solubility.

A liquid jet is produced with the aid of a pump and sucks the compressed acetylene into the jet nozzle and thus dissolves it in the liquid so rapidly that no acetylene gas phase which could undergo decomposition occurs in the reactor. The reactor used may be a jet reactor, as described in Ullmann, Vol. B4, pages 297 to 307. It should be ensured that no gas phase can build up in the reactor. The saturation of the reactor content with acetylene in the liquid phase can be kept constant over the entire course of the reaction at, as a rule, from 5 to 100%, preferably from 10 to 95%, particularly preferably from 30 to 80%, in particular from 40 to 70%. The amount of overflow per unit time which is recycled from the equilibration container to the reactor is not critical and may be from 0.01 to 2, preferably from 0.1 to 1, times the reactor content per hour. The reaction can be carried out to any desired conversion of starting material, and this can be monitored, for example, by continuous analysis of the overflow. Complete conversion of reactor content and equilibration container is also possible and is frequently desirable in order to avoid subsequent separation problems.

This process is suitable for a large number of reactions with acetylene, for example vinylation [Liebigs Anm. [sic] Chem. 601 (1956), 81–138] (reaction of acidic compounds with acetylene to give vinyl compounds), ethynylation [W. Reppe, Neue Entwicklungen auf dem Gebiet des Acetylens und Kohlenoxyds, Springer 1949, pages 23–66] (reaction of acetylene with carbonyl compounds to give alcohols) or carbonylation [W. Reppe, Neue Entwicklungen auf dem Gebiet des Acetylens und Kohlenoxyds, Springer 1949, pages 94–126] (reaction of acetylene with carbon monoxide and nucleophiles to give carboxylic acid derivatives), preferably vinylations.

EXAMPLES

Examples 1 to 8

A 6 l jet reactor was hydraulically filled with the product to be vinylated, in which the catalyst (potassium hydroxide) had been dissolved, and the pressures and temperatures stated in the table were established. A propulsive jet of about 1200 l/h was generated for the jet nozzle with the aid of a canned-motor pump, and a constant stream was recycled from the equilibration container to the reactor by means of a diaphragm pump. The acetylene feed was adjusted by means of a control in which the amount of discharge and the amount of exit gas were utilized. The course of the vinylation was monitored by hourly sampling. After the end of the reaction, the reactor content was cooled, let down and worked up.

TABLE

| No. | Product | Pressure [bar] | Temperature [°C.] | Run time [h] | Acetylene feed [l/h] | Acetylene exit gas [l/h] | Setpoint value [l/kg] | Recycling [kg/h] | Conversion [%] |
|---|---|---|---|---|---|---|---|---|---|
| 1 | n-Butanol | 18 | 160 | 22 | 390 | 28 | 10 | 4 | 99.7 |
| 2 | Cyclohexanol | 18 | 160 | 14 | 450 | 53 | 10 | 5 | 99.6 |
| 3 | Ethylene glycol | 20 | 160 | 7 | 490 | 20 | 20 | 1 | 59.0 |
| 4 | Butanediol | 19.5 | 160 | 31 | 400 | 55 | 10 | 5.3 | 92.5 |
| 5 | Imidazole | 18 | 160 | 36 | 340 | 36 | 8 | 4 | 87.1 |
| 6 | Diethylene glycol | 18 | 160 | 46 | 290 | 30 | 7 | 4 | 100 |
| 7 | Cyclohexane-dimethanol | 18 | 160 | 15 | 400 | 25 | 5 | 4 | 68.0 |
| 8 | Methyltriethylene glycol | 18 | 160 | 10 | 330 | 30 | 10 | 4 | 65.1 |

Example 9

Continuous oxidation of propionaldehyde

Propionaldehyde was oxidized with pure oxygen to propionic acid in a three-stage reactor cascade consisting of two jet reactors and a dwell tank. The reactor volume was in each case 2 l. The jet reactors were equipped with a binary nozzle in the reactor cover and a concentric immersion tube. The discharge line (overflow) of the reactors arranged one on top of the other was located at the highest point of the reactor. The product stream was let down before the phase separator, which was flushed with nitrogen as an inert gas. The jet of the binary nozzle was generated by means of a centrifugal pump. The continuous feed of 1 l/h of propionaldehyde was effected by means of a piston pump. At 60° C. and a reactor pressure of 5 bar, a conversion of more than 98% was achieved.

We claim:

1. In a batch process for carrying out a potentially explosive gas/liquid reaction in the absence of a continuous gas phase, the gaseous reactant being solubilized in a liquid phase containing the liquid reactant, the improvement which comprises:

introducing said gaseous reactant batchwise into a liquid phase solvent, which consists essentially of said liquid reactant, up to a degree of saturation of from 5 to 100% while carrying out the reaction at a temperature of from (−50°) up to 300° C. and a pressure of from 0.1 to 100 bar.

2. A process as claimed in claim 1, wherein the gaseous reactant is acetylene which is introduced batchwise into said liquid phase reactant at from 0° up to 300° C. and from 2 up to 30 bar.

3. A process for carrying out a gas/liquid reaction as claimed in claim 1, wherein the reaction is carried out at a degree of saturation of from 10 to 95%.

4. A process for carrying out a gas/liquid reaction as claimed in claim 1, wherein the reaction is carried out at a degree of saturation of from 30 to 80%.

5. A process for carrying out a gas/liquid reaction as claimed in claim 1, wherein the reaction is carried out at a degree of saturation of from 40 to 70%.

6. A process for carrying out a gas/liquid reaction as claimed in claim 1, wherein the reaction is carried out at from 10 to 25 bar.

7. A process for carrying out a gas/liquid reaction as claimed in claim 1, wherein the reaction is carried out at from 15 to 20 bar.

8. A process for carrying out a gas/liquid reaction as claimed in claim 1, wherein the reaction is carried out at from 20° to 200° C.

9. A process for carrying out a gas/liquid reaction as claimed in claim 1, wherein the reaction carried out is a vinylation, an ethynylation or a carbonylation.

10. A process for carrying out gas/liquid reaction as claimed in claim 1, wherein the reaction carried out is a vinylation.

11. A process as claimed in claim 1, wherein the solubilized gaseous reactant is selected from the group consisting of: acetylene and its higher homologs; ethylene oxide, propylene oxide and their higher homologs; acrolein; oxygen; chlorine dioxide; hydrazine; and hydrazoic acid.

12. A process a claimed in claim 1, wherein the gaseous reactant is acetylene introduced batchwise into a liquid reaction medium as required for a reaction selected from the group consisting of vinylation, ethynylation or carbonylation.

* * * * *